(12) United States Patent
Shartle

(10) Patent No.: US 6,908,593 B1
(45) Date of Patent: Jun. 21, 2005

(54) CAPILLARY FLOW CONTROL IN A FLUIDIC DIAGNOSTIC DEVICE

(75) Inventor: Robert Justice Shartle, Livermore, CA (US)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 09/541,376

(22) Filed: Mar. 31, 2000

(51) Int. Cl.[7] ............................................. G01N 21/05
(52) U.S. Cl. ................... 422/58; 422/55; 422/82.05; 422/100; 436/69; 436/164; 436/165; 436/180; 356/39; 356/246
(58) Field of Search .............................. 422/55, 58, 61, 422/82.05, 100, 102, 103; 436/69, 164, 165, 169, 180; 356/39, 246

(56) References Cited

U.S. PATENT DOCUMENTS

| | | | |
|---|---|---|---|
| 4,136,036 A | 1/1979 | Columbus | |
| 4,224,125 A | 9/1980 | Nakamura et al. | 204/195 |
| 4,254,083 A | 3/1981 | Columbus | 244/55 |
| 4,426,451 A | 1/1984 | Columbus | 436/518 |
| 4,545,382 A | 10/1985 | Higgins et al. | 128/635 |
| 4,868,129 A | 9/1989 | Gibbons et al. | 436/179 |
| 5,104,813 A * | 4/1992 | Besemer et al. | 422/100 |
| 5,222,808 A * | 6/1993 | Sugarman et al. | 366/274 |
| 5,223,219 A * | 6/1993 | Subramanian et al. | 210/451 |
| 5,230,866 A | 7/1993 | Shartle et al. | 422/103 |
| 5,472,603 A | 12/1995 | Schembri | 210/380.1 |
| 5,627,041 A | 5/1997 | Shartle | 435/7.24 |
| 5,700,695 A | 12/1997 | Yassinzadeh et al. | 436/180 |
| 5,736,404 A | 4/1998 | Yassinzadeh et al. | 436/52 |
| 5,885,527 A | 3/1999 | Buechler | |
| 5,912,134 A | 6/1999 | Shartle | 435/7.24 |
| 5,997,817 A | 12/1999 | Crismore et al. | 422/58 |
| 6,001,307 A | 12/1999 | Naka et al. | 422/81 |
| 6,084,660 A * | 7/2000 | Shartle | 356/246 |
| 6,261,519 B1 * | 7/2001 | Harding et al. | 422/58 |
| 6,325,975 B1 * | 12/2001 | Naka et al. | 422/50 |

FOREIGN PATENT DOCUMENTS

| | | |
|---|---|---|
| EP | 0803288 A | 10/1997 |
| EP | 0974840 A | 1/2000 |
| EP | 974840 * | 1/2000 |
| WO | WO 95/12117 | 5/1995 |
| WO | WO 97/18464 | 5/1997 |
| WO | WO 9807019 A | 2/1998 |
| WO | WO 9946045 A | 9/1999 |

OTHER PUBLICATIONS

European Patent Office Search Report dated Sep. 4, 2003.

* cited by examiner

Primary Examiner—Maureen M. Wallenhorst

(57) ABSTRACT

A medical diagnostic device for measuring an analyte concentration or property of a biological fluid includes capillary flow channels to convey a sample of the fluid from an inlet to a branching point, and then to a measurement area and, alternatively, through a bypass channel to an overflow region. A first stop junction stops fluid flow after it enters the measurement area. The bypass channel has a capillary dimension in at least one direction. A second stop junction, in the bypass channel, has boundary region that has a dimension that is greater in that direction and forms an angle that points toward the branching point. With this construction, the second stop junction initially prevents flow to the overflow region, but permits the flow after the measurement area is filled. The device is particularly suited for measuring coagulation time of blood.

10 Claims, 5 Drawing Sheets

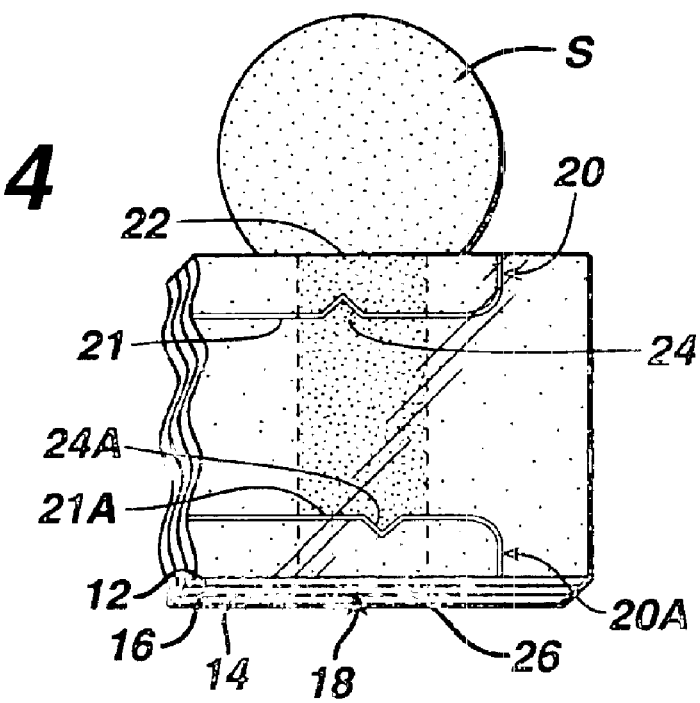
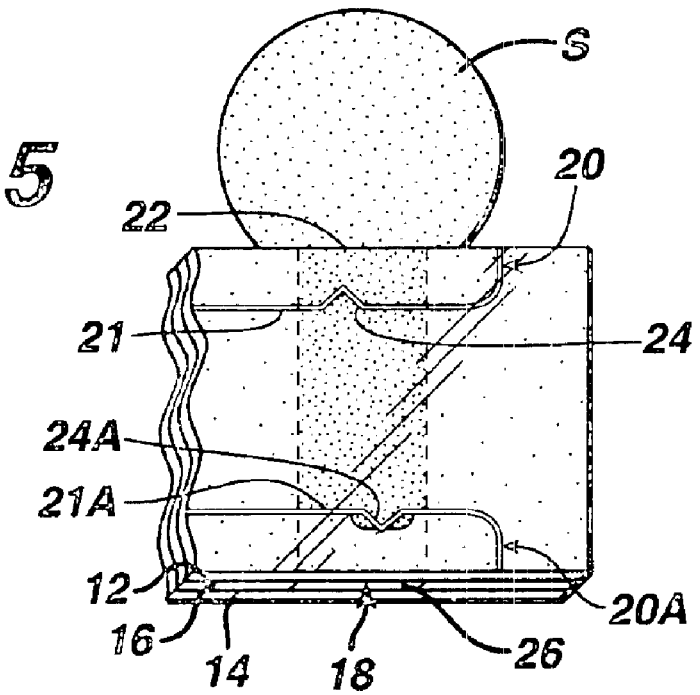

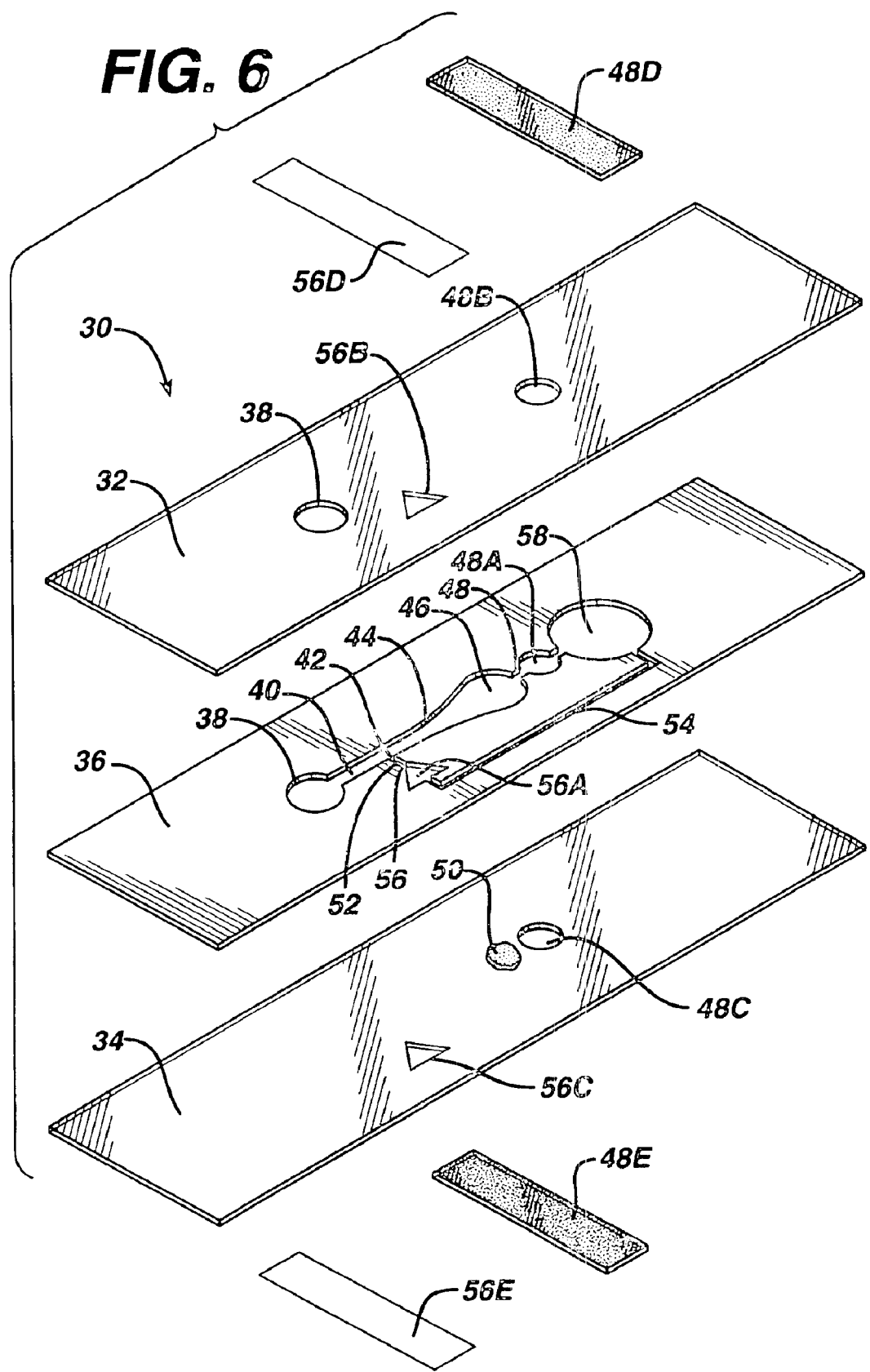

CAPILLARY FLOW CONTROL IN A FLUIDIC DIAGNOSTIC DEVICE

CROSS-REFERENCE TO PRIOR APPLICATION

This application relates to U.S. application Ser. Nos. 09/333,765, filed Jun. 15, 1999, now U.S. Pat. No. 6,521,182, issued on Feb. 18, 2003; and 09/354,995, filed Jul. 16, 1999, now U.S. Pat. No. 6,084,660, issued on Jul. 4, 2000.

BACKGROUND OF THE INVENTION

1. Field of the Invention

This invention relates to a medical diagnostic device that includes an element for controlling fluid flow through the device; more particularly, to a device that facilitates fluid flow through a stop junction.

2. Description of the Related Art

A variety of medical diagnostic procedures involve tests on biological fluids, such as blood, urine, or saliva, to determine an analyte concentration in the fluid. The procedures measure a variety of physical parameters—mechanical, optical, electrical, etc.,—of the biological fluid.

Among the analytes of greatest interest is glucose, and dry phase reagent strips incorporating enzyme-based compositions are used extensively in clinical laboratories, physicians' offices, hospitals, and homes to test samples of biological fluids for glucose concentration. In fact, reagent strips have become an everyday necessity for many of the nation's estimated 16 million people with diabetes. Since diabetes can cause dangerous anomalies in blood chemistry, it can contribute to vision loss, kidney failure, and other serious medical consequences. To minimize the risk of these consequences, most people with diabetes must test themselves periodically, then adjust their glucose concentration accordingly, for instance, through diet, exercise, and/or insulin injections. Some patients must test their blood glucose concentration as often as four times or more daily.

One type of glucose measurement system operates electrochemically, detecting the oxidation of blood glucose on a dry reagent strip. The reagent generally includes an enzyme, such as glucose oxidase or glucose dehydrogenase, and a redox mediator, such as ferrocene or ferricyanide. This type of measurement system is described in U.S. Pat. No. 4,224,125; issued on Sep. 23, 1980, to Nakamura et al.; and U.S. Pat. No. 4,545,382, issued on Oct. 8, 1985, to Higgins et al., incorporated herein by reference.

Hodges et al., WO 9718464 A1, published on May 22, 1997, discloses an electrochemical device for measuring blood glucose that includes two metallized polyethylene terephthalate (PET) layers sandwiching an adhesive-coated PET intermediate layer. The metallized layers constitute first and second electrodes, and a cutout in the adhesive-coated layer defines an electrochemical cell. The cell contains the reagent that reacts with the glucose in a blood sample. The device is elongated, and the sample is introduced at an inlet on one of the long sides.

The electrochemical devices for measuring blood glucose that are described in the patents cited above, as well as other medical diagnostic devices used for measuring analyte concentrations or characteristics of biological fluids, generally share a need to transport the fluid from a sample inlet to one or more other sections of the device. Typically, a sample flows through capillary channels between two spaced-apart surfaces. A number of patents, discussed below, disclose medical diagnostic devices and include descriptions of various methods to control the flow of the sample.

U.S. Pat. No. 4,254,083, issued on Mar. 3, 1981, to Columbus, discloses a device that includes a sample inlet configured to facilitate movement of a drop of fluid sample into the device, by causing a compound meniscus to form on the drop. (See also U.S. Pat. No. 5,997,817, issued on Dec. 7, 1999 to Crismore et al.)

U.S. Pat. No. 4,426,451, issued on Jan. 17, 1984 to Columbus, discloses a multi-zone fluidic device that has pressure-actuatable means for controlling the flow of fluid between the zones. His device makes use of pressure balances on a liquid meniscus at the interface between a first zone and a second zone that has a different cross section. When both the first and second zones are at atmospheric pressure, surface tension creates a back pressure that stops the liquid meniscus from proceeding from the first zone to the second. The configuration of this interface or "stop junction" is such that the liquid flows into the second zone only upon application of an externally generated pressure to the liquid in the first zone that is sufficient to push the meniscus into the second zone.

U.S. Pat. No. 4,868,129, issued on Sep. 19, 1989 to Gibbons et al., discloses that the back pressure in a stop junction can be overcome by hydrostatic pressure on the liquid in the first zone, for example by having a column of fluid in the first zone.

U.S. Pat. No. 5,230,866, issued on Jul. 27, 1993 to Shartle et al., discloses a fluidic device with multiple stop junctions in which the surface tension-induced back pressure at the stop junction is augmented; for example, by trapping and compressing gas in the second zone. The compressed gas can then be vented before applying additional hydrostatic pressure to the first zone to cause fluid to flow into the second zone. By varying the back pressure of multiple stop junctions in parallel, "rupture junctions" can be formed, having lower maximum back pressure.

U.S. Pat. No. 5,472,603, issued on Dec. 5, 1995 to Schembri (see also U.S. Pat. No. 5,627,041), discloses using centrifugal force to overcome the back pressure in a stop junction. When flow stops, the first zone is at atmospheric pressure plus a centrifugally generated pressure that is less than the pressure required to overcome the back pressure. The second zone is at atmospheric pressure. To resume flow, additional centrifugal pressure is applied to the first zone, overcoming the meniscus back pressure. The second zone remains at atmospheric pressure.

U.S. Pat. No. 6,011,307, issued on Dec. 14, 1999, to Naka et al., published on Oct. 29, 1997, discloses a device and method for analyzing a sample that includes drawing the sample into the device by suction, then reacting the sample with a reagent in an analytical section. Analysis is done by optical or electrochemical means. In alternate embodiments, there are multiple analytical sections and/or a bypass channel. The flow among these sections is balanced without using stop junctions.

U.S. Pat. No. 5,700,695, issued on Dec. 23, 1997 to Yassinzadeh et al., discloses an apparatus for collecting and manipulating a biological fluid that uses a "thermal pressure chamber" to provide the driving force for moving the sample through the apparatus.

U.S. Pat. No. 5,736,404, issued on Apr. 7, 1998, to Yassinzadeh et al., discloses a method for determining the coagulation time of a blood sample that involves causing an end of the sample to oscillate within a passageway. The oscillating motion is caused by alternately increasing and decreasing the pressure on the sample.

None of the references discussed above suggest a device in which a flow channel has a stop junction that is angular in the flow direction.

SUMMARY OF THE INVENTION

This invention provides a medical device for measuring an analyte concentration or property of a biological fluid. This embodiment of the device comprises a) a sample inlet for introducing a sample of the biological fluid into the device;

b) a first capillary channel for conveying the sample from the inlet to a branching point;

c) a capillary connecting channel for conveying a first part of the sample from the branching point through a measurement area, in which is measured a physical parameter of the sample that is related to the analyte concentration or property of the fluid, and to a first stop junction;

d) a capillary bypass channel for conveying a second part of the sample in a first direction from a first region, proximate to the branching point, to an overflow region, distal to the branching point, the first region having a capillary dimension in a second direction substantially perpendicular to the first direction;

e) a second stop junction in the bypass channel, comprising a boundary region that i) separates the first and overflow regions, ii) has a second predetermined dimension in the second direction that is greater than the capillary dimension, and iii) forms an angle that points toward the first region, whereby any excess sample that enters the sample inlet will pass through the second stop junction into the overflow region.

Devices of the present invention provide, in a capillary flow channel of the device, a stop junction that is angular in the flow direction. Such a stop junction can be designed with readily-controlled break-through pressure. Note that in the present specification and the figures, capillaries are shown bounded by parallel plates. In that case, the "second direction". which has the capillary dimension, is uniquely determined. Alternatively, capillaries of the invention could be cylindrical. In that case, the second direction is radial, in a planar circle, or disk, that is perpendicular to the direction of fluid flow.

BRIEF DESCRIPTION OF THE DRAWINGS

FIGS. 2–5 depict the flow of a fluid in part of a device of this invention.

FIG. 6 is an exploded perspective view of a device of this invention.

DETAILED DESCRIPTION OF THE INVENTION

When fluid flows through a channel, a discontinuity in channel cross section can form a "stop junction," which can stop the fluid flow, as described in U.S. Pat. Nos. 4,426,451; 5,230,866; and 5,912,134, incorporated herein by reference. The stop junction results from surface tension that creates a back pressure that stops the fluid meniscus from proceeding through the discontinuity. The stop junction is weakened, and flow thereby enhanced, when the leading edge of the meniscus encounters the vertex of an acute angle and is then stretched along the arms of the angle. This may be described as the angle "pointing" in a direction opposite to the direction of fluid flow.

This invention relates to a medical diagnostic device that has a flow channel with a stop junction. The stop junction is angular in the direction of flow, which permits fluid in the channel to break through the stop junction when there is a predetermined pressure difference across the stop junction. The advantages of such a controlled break-through stop junction are apparent from the description that follows.

Figure 1:
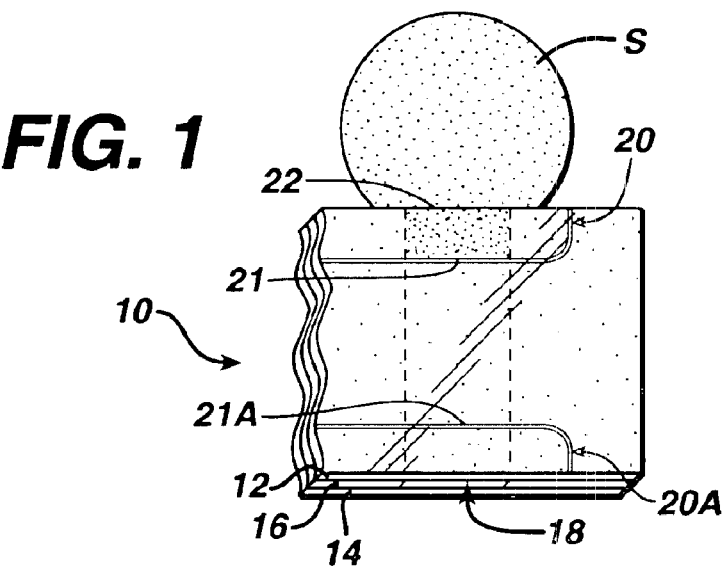
FIG. 1 depicts the operation of a stop junction in a medical device.

FIG. 1 depicts part of a medical diagnostic strip 10 that is a multilayer sandwich. Top layer 12 and bottom layer 14 sandwich intermediate layer 16. A cutout in intermediate layer 16 forms channel 18. Lines 20 and 20A are scored into the bottom surface of layer 12 and form in channel 18 stop junctions 21 and 21A, respectively. Thus, sample S, introduced into channel 18 at sample inlet 22, stops when it reaches stop junction 21.

Figure 2:
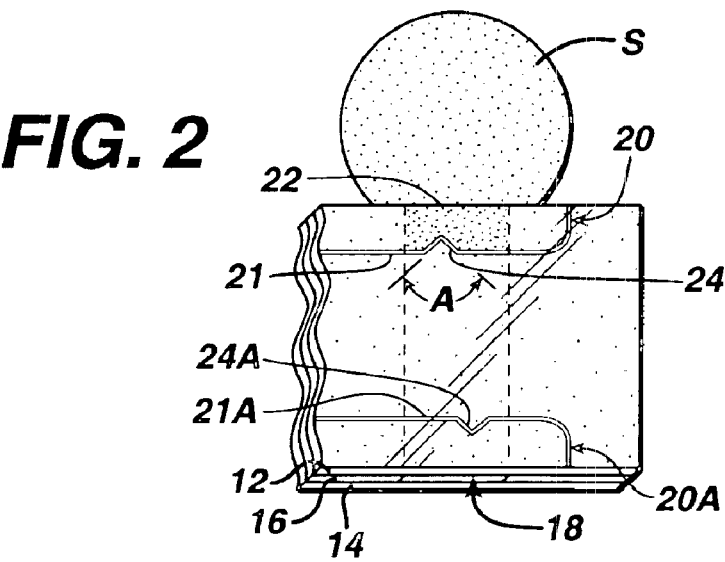
Figure 3:
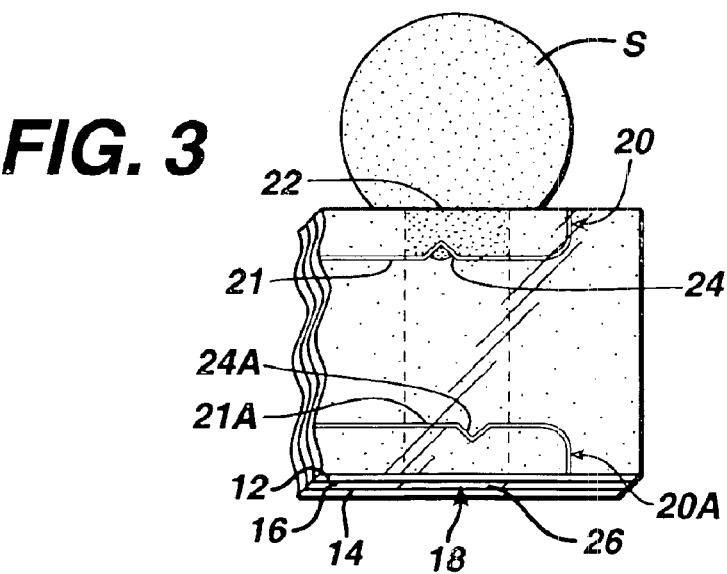

FIGS. 2 and 3 depict the part of a medical diagnostic strip of FIG. 1 in which stop junctions 21 and 21A have been modified by adding serrations 24 and 24A, respectively. Serration 24 forms an acute angle A that "points" toward sample inlet 22. FIGS. 2 and 3 depict sample S just before and just after it breaks through stop junction 21, respectively. Note that the breakthrough occurs first at the vertex that points opposite to the direction of fluid flow. The effectiveness of the serration in enhancing flow through a stop junction in a capillary channel depends on the angle and the length of the legs that form the angle. The smaller the angle and the longer the legs, the greater the effectiveness of the serration. Thus, if the angle is small and the legs long, only a small hydraulic pressure differential across the scored region will cause the sample to flow through it. Preferably, angle A is less than about 90° and its axis of symmetry is aligned with the direction of flow in the channel.

Stop junction 21A has an angle that points toward end 26 of channel 18 that is opposite inlet 22, and it would have reduced resistance to the flow of sample that entered end 26. FIGS. 4 and 5 depict the flow of sample through channel 18 after it has broken through stop junction 21. In FIG. 4, the sample is stopped at stop junction 21A. In FIG. 5, sample has passed through stop junction 21A at its two ends. The breakthroughs occur there, because although the angles at the two ends are greater than 90°, they are smaller than the angle (i.e., the supplement of. the angle that points toward 26) at the center of serration 24A. A short time after the sample reaches the position shown in FIG. 5, the sample will pass through stop junction 21A across the entire width of channel 18.

FIG. 6 is an exploded perspective view of an embodiment of the present invention. The diagnostic device 30 has a top layer 32 and bottom layer 34 sandwiching intermediate layer 36. Elements of the device are formed by the layers, together with cutouts them. Depicted in FIG. 6 are sample inlet 38, formed by coaligned holes in intermediate layer 66 and top layer 32; first capillary channel 40, for conveying sample from sample inlet 38 to branching point 42; and capillary connecting channel 44, for conveying sample through measurement area 46 to a first stop junction 48. Stop junction 48 is formed by the intersection of the capillary neck, at the end of measurement area 46, and the coinciding holes 48A, 48B, and 48C in intermediate layer 36, top layer 32, and bottom layer 34, respectively. Holes 48A, 48B, and 48C are conveniently punched in a single operation when the layers are together. In a less-preferred embodiment, only two holes are needed. Thus 48B or 48C could be omitted.

Measurement area 46 preferably contains a reagent 50. Cutout 58 is part of a bladder that includes the adjoining regions of top layer 32 and bottom layer 34. Capillary bypass channel 52 provides an alternate path from branching point 42 to overflow region 54. A stop junction 56 in bypass channel 52 impedes flow into overflow region 54. Stop junction 56 is formed by the intersection of capillary bypass channel 52 and the coinciding holes 56A, 56B, and 56C in intermediate layer 36, top layer 32, and bottom layer 34, respectively. (Either hole 56B or 56C can be omitted). Note that stop junctions 48 and 56 also require seals 48D, 48E, and 56D, 56E, respectively.

Figure 7:
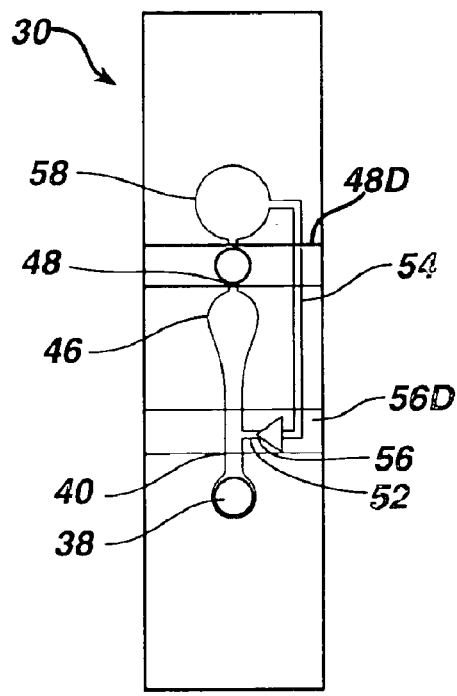
FIG. 7 is a plan view of the device of FIG. 6.

FIG. 7 is a top plan view of the device of FIG. 6. The device depicted in FIGS. 6 and 7 is particularly well suited for measuring blood-clotting time—"prothrombin time" or "PT time"—and details regarding such a device appear below. The modifications needed to adapt the device for other medical diagnostic applications require no more than routine experimentation. In operation, sample is applied to sample port 38 after bladder 58 has been compressed. Clearly, the region of top layer 32 and/or bottom layer 34 that adjoins the cutout for bladder 58 must be resilient, to permit bladder 58 to be compressed. When the bladder is released, suction draws sample through first capillary channel 40 to branching point 42 and through capillary connecting channel 44 to measurement area 46. In order to ensure that measurement area 46 can be filled with sample, the volume of bladder 58 is preferably at least about equal to the combined volume of first channel 40, connecting channel 44, capillary bypass channel 52, and measurement area 46. If the measurement method is optical, and the measurement area 46 is to be illuminated from below, bottom layer 34 must be transparent where it adjoins measurement area 46. For a PT test, reagent 50 contains thromboplastin that is free of bulking reagents normally found in lyophilized reagents.

As shown in FIGS. 6 and 7, sample is drawn into the device by suction, caused by decompression of bladder 88. When the sample reaches stop junction 48, sample flow stops. For PT measurements, it is important to stop the flow of sample as it reaches that point to permit reproducible "rouleaux formation"—the stacking of red blood cells—which is an important step in monitoring blood clotting using the present invention.

Figure 7A:
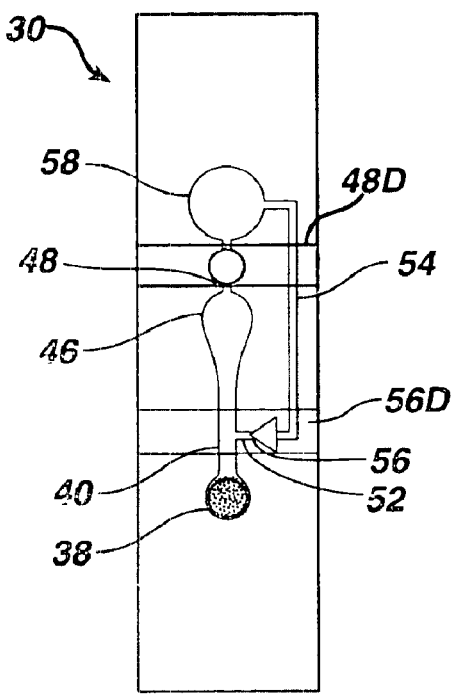
FIGS. 7A, 7B, and 7C depict sample filling the device of FIG. 6.
Figure 7B:
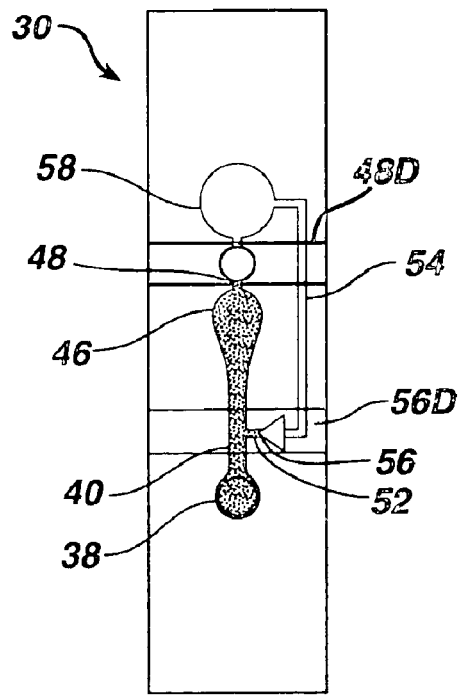
Figure 7C:
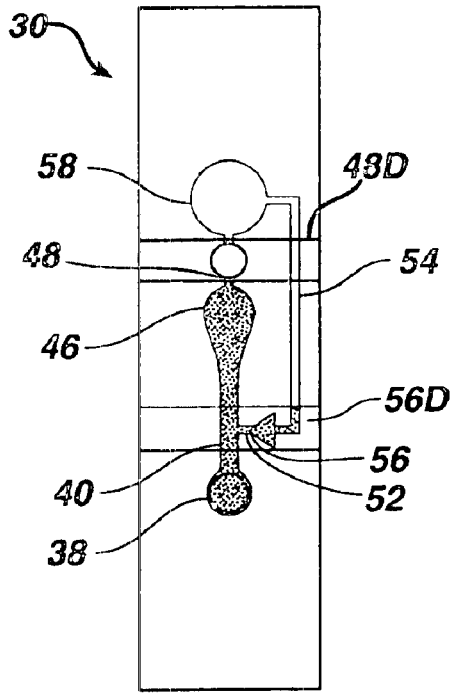

The function and operation of the bypass channel can be understood by referring to FIGS. 7A, 7B, and 7C which depict a time sequence during which a sample is drawn into device 30 for the measurement.

FIG. 7A depicts the situation after a user has applied a sample to the strip, while bladder 58 is compressed. This can be accomplished by applying one or more drops of blood.

FIG. 7B depicts the situation after the bladder is decompressed. The resulting reduced pressure in the first channel 40 and connecting channel 44 draws the sample initially into the measurement area 46. When the sample reaches stop junction 48, the sample encounters a back pressure that causes it to stop and causes additional sample to be drawn into the bypass channel toward stop junction 56. Note that stop junction 56 is "weaker" than stop junction 48, because it has an angle A that points toward branching point 42. (See FIGS. 1–5). Thus weak stop junction 56 performs two functions. It first impedes the flow of sample into overflow region 54, thus permitting measurement area 46 to fill rapidly. Second, it permits any excess sample to flow through it (after measurement area 46 is full) to relieve any pressure difference remaining on the two sides of stop junction 48. Such a pressure difference could cause sample to "leak" through stop junction 48, causing movement of sample through the measurement area, which is undesirable, for the reason discussed earlier.

FIG. 7C depicts the situation when an equilibrium has been established among the pressures on the sample surfaces—atmospheric pressure on the sample in inlet 38 and the pressure on the free surfaces in overflow region 54 and stop junction 48.

Figure 8:
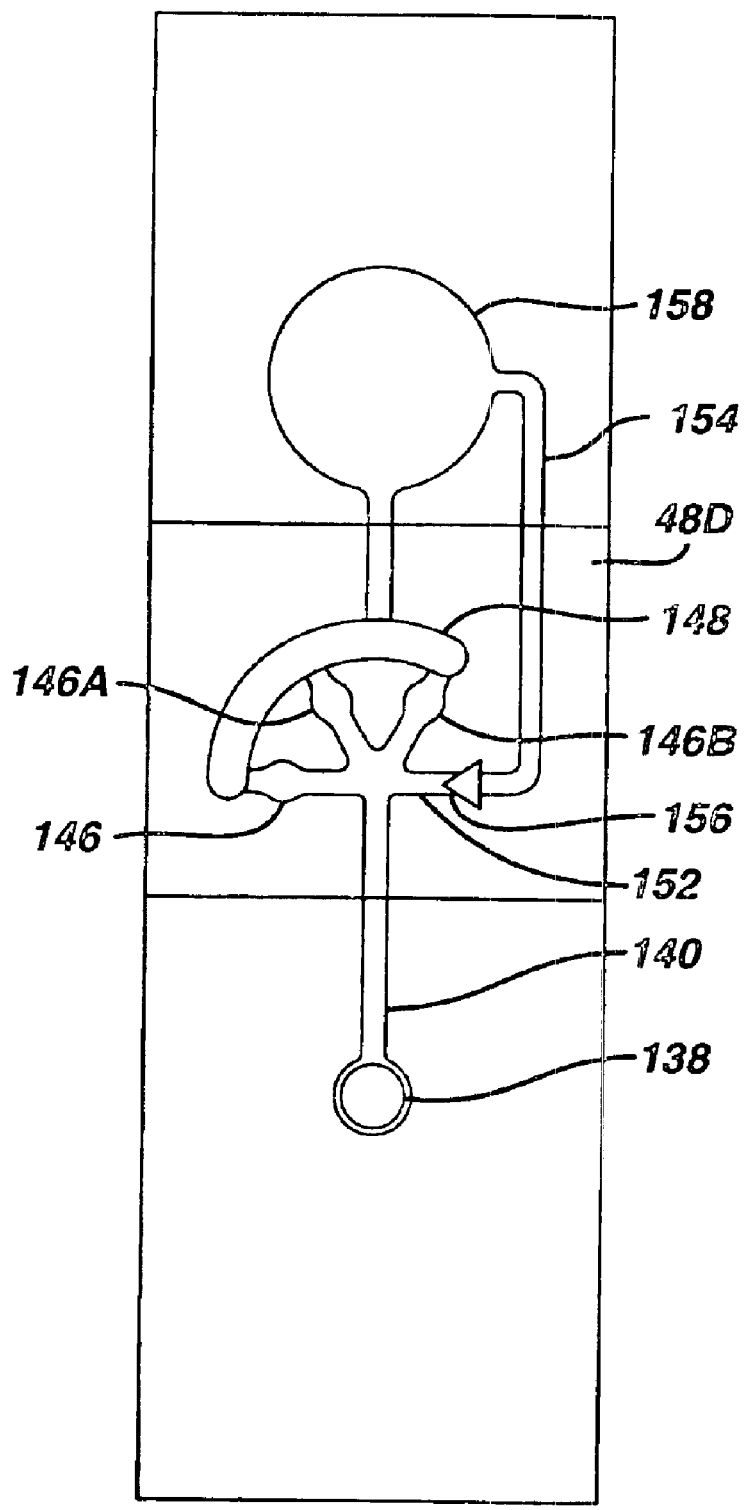
FIG. 8 is a plan view of a preferred embodiment of this invention, which includes three measurement areas.

FIG. 8 depicts a preferred embodiment of the present device that includes three measurement areas. For a PT test, measurement area 146 contains thromboplastin. Preferably, measurement areas 146A and 146B contain controls, more preferably, the controls described below. Area 146A contains thromboplastin, bovine eluate,. and recombinant Factor VIIa. The composition is selected to normalize the clotting time of a blood sample by counteracting the effect of an anticoagulant, such as warfarin. Measurement area 146B contains thromboplastin and bovine eluate alone, to partially overcome the effect of an anticoagulent. Thus, three measurements are made on the strip. PT time of the sample, the measurement of primary interest, is measured on area 146. However, that measurement is validated only when measurements on areas 146A and 146B yield results within a predetermined range. If either or both of these control measurements are outside the range, then a retest is indicated. Extended stop junction 148 stops flow in all three measurement areas. Stop junction 156, in bypass channel 152, functions as described above.

Additional details on this embodiment of the invention appear in copending U.S. patent application Ser. No. 09/333,765, filed on Jun. 15, 1999, and incorporated herein by reference.

I claim:

1. A medical diagnostic device for measuring at least one of an analyte centration and a property of a biological fluid, comprising
   a) a sample inlet for introducing a sample of the biological fluid into the medical diagnostic device;
   b) a first capillary channel for conveying the sample from the sample inlet to a branching point;
   c) a capillary connecting channel for conveying a first part of the sample from the branching point through a measurement area, in which is measured a physical parameter of the sample that is related to the at least one of the analyte concentration and property of the biological fluid, and, thereafter, to a first stop junction;
   d) a capillary bypass channel for conveying a second part of the sample in a first direction from a first region, proximate to the branching point, to an overflow region, distal to the branching point, the first region having a capillary dimension in a second direction substantially perpendicular to the first direction;
   e) a second stop junction in the capillary bypass channel, comprising a boundary region that
      i) separates the first region and overflow region,
      ii) has a second predetermined dimension in the second direction that is greater than the capillary dimension, and
      iii) is triangular in shape with two legs that define an angle of less than 90 degrees that points toward the first region, whereby excess sample that enters the sample inlet will pass through the second stop junction into the overflow region; and wherein the second stop junction impedes sample flow into the overflow region while the first part of the sample is being conveyed through the measurement area and the second stop junction is weaker than the first stop junction such that the excess sample passes through the second stop junction into the overflow region only after sample has filled the measurement area.

2. The medical diagnostic device of claim 1, further comprising
   a suction device, in fluid communication with the first and second stop junctions, for drawing the sample from the sample inlet toward the first and second stop junctions.

3. The medical diagnostic device of claim 2, in which the medical diagnostic device further comprises a first layer and second layer, at least one of which has a resilient region over at least a part of its area, separated by an intermediate layer, and in which
   a) cutouts in the layers form, with the layers, the sample inlet, first capillary channel, capillary connecting channel, measurement area, and capillary bypass channel;
   b) the suction device comprises a bladder that
      i) is distal from the sample inlet,
      ii) comprises at least a part of the resilient region, and
      iii) has a volume that is at least about equal to the combined volume of the first capillary channel, measurement area, capillary connecting channel, and capillary bypass channel, and
   c) the first and second stop junctions comprise coinciding holes in the first, second and intermediate layers that are sandwiched by a third layer and a fourth layer.

4. The medical diagnostic device of claim 3 in which at least one of the first and second layer is substantially transparent adjoining the measurement area, and the physical parameter that is measured is optical transmission.

5. The medical diagnostic device of claim 3 in which the physical parameter of the sample undergoes a change in the measurement area.

6. The medical diagnostic device of claim 5 in which the measurement area contains a composition that facilitates blood clotting, the biological fluid is whole blood, and the property being measured is prothrombin time.

7. The medical diagnostic device of claim 6 in which the composition comprises thromboplastin.

8. The medical diagnostic device of claim 6 further comprising at least one additional fluidic path from the branching point to the bladder, each such additional path including a corresponding measurement area and stop junction.

9. The medical diagnostic device of claim 8 in which a first additional path includes corresponding measurement area that overcomes the effect of an anticoagulant and a second additional path includes a corresponding measurement area that partially overcomes the effect of an anticoagulant.

10. The medical diagnostic device of claim 9 in which the corresponding measurement area of the first additional path comprises thromboplastin, bovine eluate, and recombinant Factor VIIa and the corresponding measurement area of the second additional path comprises thromboplastin and bovine eluate.

* * * * *